United States Patent [19]

Johnson, Jr.

[11] Plant 4,250

[45] May 9, 1978

[54] STRAWBERRY PLANT

[75] Inventor: Harold A. Johnson, Jr., Watsonville, Calif.

[73] Assignee: Driscoll Strawberry Associates, Inc., Watsonville, Calif.

[21] Appl. No.: 787,809

[22] Filed: Apr. 15, 1977

[51] Int. Cl.[2] ..... A01H 5/03

[52] U.S. Cl. ..... Plt./49

[58] Field of Search ..... Plt./49

*Primary Examiner*—Robert E. Bagwill

*Assistant Examiner*—James R. Feyrer

[57] ABSTRACT

A new and distinct everbearing strawberry plant particularly characterized by presenting occasional basal foliar bracts, having high vigor and heavy bearing when chilled and having darker foliage and greater strength than normal for an everbearer. Compared to that of Driscoll, U.S. Plant Pat. No. 3,529, fruit of the instant plant is generally wider than long, firmer, darker on the outside and whiter on the inside.

1 Drawing Figure

This invention relates to a new and distinct variety of strawberry plant which is the result of a cross of the everbearing Driscoll Strawberry Associates, Inc. (Driscoll) variety E15 and U.S. Plant Pat. No. 3,123.

The seedlings resulting from the aforementioned cross were grown and asexually multiplied in Shasta County, Calif., and tested in the fruiting beds on the property of grower members of Driscoll. Clones of the seedlings were also held at the Propagation Nursery in Shasta County. One plant was selected from the aforementioned group of seedlings and further asexually reproduced in the Shasta County Nursery of Driscoll. Tests followed in various parts of California during intervening seasons on various properties of grower members of Driscoll. These tests indicated the merits of the novel plant and resulted in its selection as a promising test variety.

FIG. 1 of the accompanying drawing illustrates plant parts of the new variety, typical in size, shape and color. Also shown in the accompanying drawing is a berry in cross section illustrating flesh color and a characteristic core cavity.

The inflorescence illustrates typical branching and relative size during July. The leaf shown is typical in appearance and size with a basal bract present which is not uncommon. The flower pictured is typical of a primary and larger secondary flowers. The runner transplant crown is medium to large in size as it comes from the nursery and produces a vigorous young plant in the spring with crown crop berries of medium size. This variety has the ability to give a large total production even when dug in late January and February and transplanted in the central coast region. However, the transplant does require chilling before it can produce a plant vigorous enough to support a strong spring, summer and fall crop. The plant is considered a strong one in comparison to most everbearers grown by Driscoll.

The primary berries from the crown and main crop are medium to large in size, are generally smooth, not furrowed, with a good gloss and appearance. Subsequent crops have secondary and tertiary fruit that are smaller, but maintain an acceptable commercial fruit size if the plant maintains adequate vigor. The cropping starts with a crown crop in late April and the main crop in late May and early June, and continues until the fall rains. The peaks in this production usually occur in July and late August, depending on when the planting took place. The cropping during the second fruiting year is typical of most everbearers grown in central California in that it crops later than spring varieties, but maintains production throughout the summer and early fall.

This novel plant of the present invention is distinguished from other varieties by its flowers, fruit and plant characteristics. It is distinguished by its dark plant and is a strong plant considering that it is an everbearer. It has the ability to produce a stronger, darker plant with more total production than that of Driscoll, U.S. Plant Pat. No. 3,529 (E18). The number of crowns per plant and the total number of leaves per plant is greater on the new variety. The leaflet size is similar, but the serrations of individual leaflets are more abundant and deeper on the new variety. The petiolule of the central leaflet is longer than that of E18 if both are grown and measured under uniform conditions. Bracts are often present on the petioles of both varieties. The new variety produces more runners per plant if each are given the same chilling.

The total length of the inflorescence and the common peduncle is longer on the new variety. The type of branching of the inflorescence is similar in that the pedicel holding the primary berry quickly originates from the axil of secondary peduncles, but this pedicel may originate from one of the peduncles. Two pedicels are often fused together which is not common on the E18.

The new variety is distinct from most varieties, as well as E18, in that hair on pedicels 20 mm from the berry are mostly at a 45° angle on the pedicel while that of E18 is held irregularly parallel to the pedicel. The fruit size is similar to E18, but under many conditions, the fruit size of secondary and tertiary berries is greater on the new variety. Both varieties have exserted seed, but the new variety is less prone to produce fruit that develop seed that is extremely exserted and which give the fruit a seedy, poor appearance. The fruit shapes of the new variety and E18 are different in that the primaries of the main crop of the new variety are often conic with an acute apex, as pictured in the drawing. This apex may be lighter in color than the remainder of the berry even though the seed at the apex is normal. Some inflorescence of the new variety produce a multiple apex on each berry giving the fruit a wedged cockscomb appearance when observing the fruit from the side. The outside color of the new variety is darker, but the inside is lighter than E18. Both varieties have a large calyx with overlapping sepals having margins that are often serrated. The color of individual sepals is darker on both sides of the new variety.

Both this variety and E18 produce fruit that are not necked, but have rounded shoulders to the fruit with the total width often greater than the length. This greater width than length is more abundant on the new variety than E18. The length is usually greater than the width on the E18. The core size would be considered small and equal to that of E18. The flesh and epidermis of the new variety is considered firm, making it valuable for interstate shipments. Some berries may have an area between calyx and seed that become white and is noticeable. This area, however, is not necked and does not influence the fruit shape. The dessert quality of the new variety is good, the flavor panel ratings, however, are not as good as E18 which is outstanding.

The new variety is moderately susceptible to mildew but, as presently known, it has not been seriously infected with Mycrosphaerella leaf spot. It has not been completely tested against Verticillium and Red Stele diseases. As a seedling and selection, this variety withstood the natural invasions of certain virus components found in central California without losing its ability to produce. There is generally no aroma peculiar to the flesh of this new variety.

The varietal characteristics of the novel plant described below in detail were observed mainly during the first fruiting season, but reference is also made to the appearance during the second fruiting year. Observations were made in the Watsonville area of California which is a cool coastal area near the Pacific Ocean. The color terminology is in accordance with Ridgway Color Standards and Nomenclature (1912 Edition).

Plants: Medium, vigorous if given ample chilling before being planted and given adequate soil nutrition and have an extensive root system producting multiple crowns by the end of the first fruiting season.

Leaves: Medium in size. Central leaflet is usually 5 to 6 cm long and 5 to 6 cm wide. Petioles are abundant for an everbearer. Petiolules are long, averaging 8 mm, but may reach 10 mm. Bracts are often present on the petioles. Leaflet color is dark, slightly rugose and mostly cupped upward from the central vein to the margin. Leaflet serrations are deep. The upper side of the leaflet is Dark Cress Green, Plate XXXI.

Runners: Vigorous and considered a consistent runner producer at the nursery, but not heavy enough in the fruiting beds to be a problem.

Inflorescence: Medium in length, mostly 20 to 30 cm. Flowers are especially visible above the plant during the late spring. The common peduncle is medium to long in length, 15 to 20 cm. Secondary peduncles are mostly two, but may be three or four in number. Primary berries usually ripen before secondaries but the difference in size is not great. The diameter of primary berries is medium to large, 30 to 35 mm. Petals are mostly five and six in number. The hair on pedicels 20 mm from the fruit makes an angle with the pedicel that averages about 45°. Pedicel holding the primary berry originates mainly at the axil of secondary peduncles, but may originate from one of the peduncles near the axil. Two pedicels are often fused together. Anthers produce an abundance of pollen except during the early spring of the second fruiting year.

Fruit: Crown crop berries are mostly medium in size. The main crop is consistently larger. Primaries are wider than the length, averaging 35 mm long and 40 mm wide. The shape is mostly conic to short wedge as described in the USDA Bulletin 1043. Most primaries have a distinct pointed apex. The surface is smooth, not furrowed, becoming malformed only when poor pollinization occurs during cold, wet periods. There may be more than one apex giving a cockscomb outline to the fruit. The shoulders near the calyx are broad, not necked. There may be white areas on the epidermis between the seed and the calyx. The flesh and epidermis are firm and the seeds are slightly exserted. The seeds are yellow if not exposed to the sun, but darken quickly if exposed. The berry has a high dessert quality when ripe. The fruit surface color is Carmine, Plate I, and the flesh is Scarlet, Plate I, and the core is White. The fruit surface color is uniform and maintains a high gloss even after a long shipment and storage.

Calyx: Large in diameter in relationship to fruit size, 25 to 40 mm. Sepals are abundant and overlap. Sepals vary in shape from elliptical to ovate and obovate and are often serrated at the margins.

I claim:

1. The new and distinct variety of strawberry plant herein described and illustrated, and identified by the characteristics enumerated above.

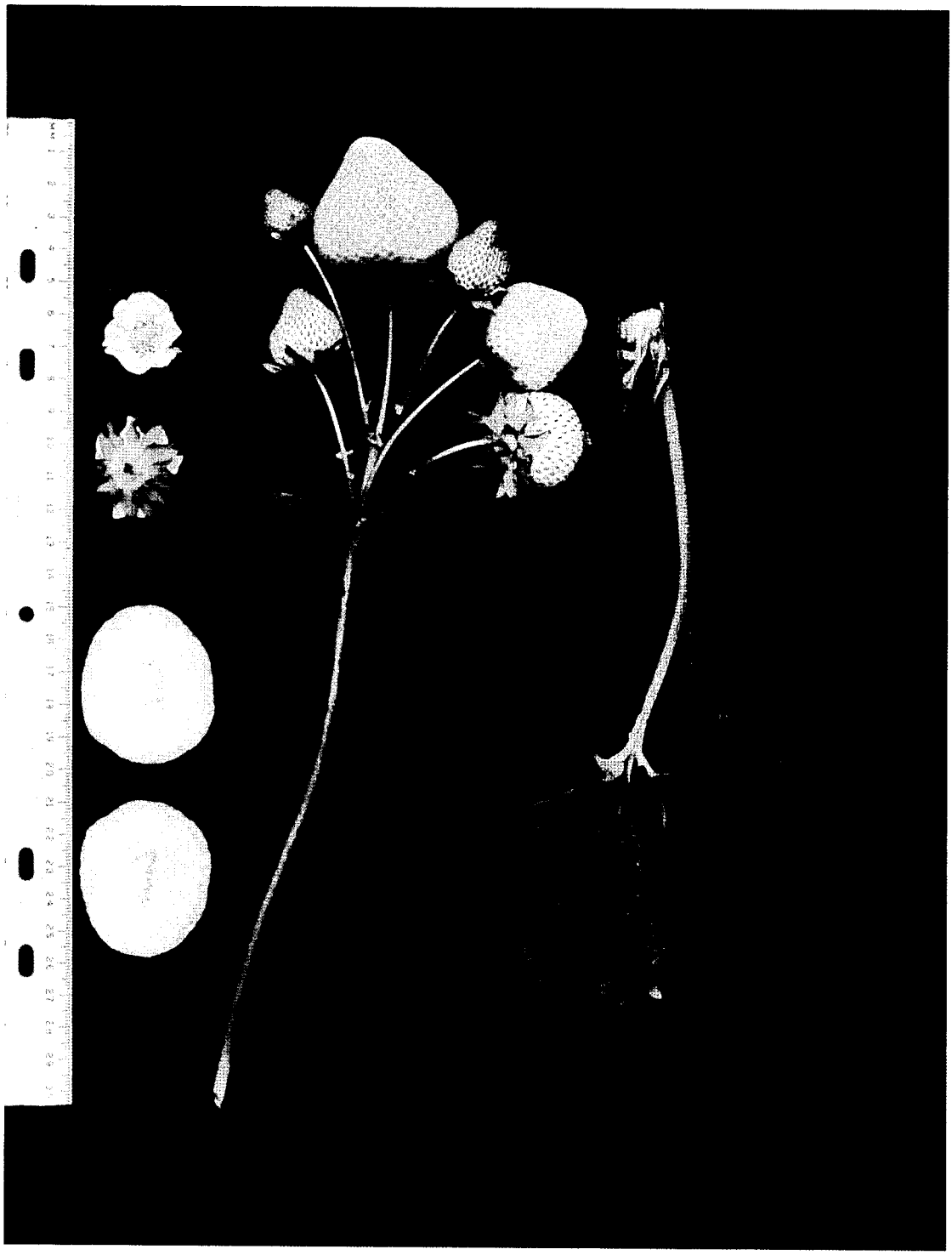

* * * * *